United States Patent [19]

Atadan

[11] Patent Number: 5,218,144

[45] Date of Patent: Jun. 8, 1993

[54] PROCESS FOR THE MANUFACTURE OF ADIPIC ACID

[75] Inventor: Erdem M. Atadan, Wilmington, Del.

[73] Assignee: E. I. du Pont de Nemours and Company, Wilmington, Del.

[21] Appl. No.: 944,997

[22] Filed: Sep. 15, 1992

Related U.S. Application Data

[63] Continuation-in-part of Ser. No. 804,559, Dec. 10, 1991, abandoned.

[51] Int. Cl.$^5$ .................... C07C 51/12; C07C 51/10
[52] U.S. Cl. ..................... 562/517; 562/522; 562/591
[58] Field of Search ............... 562/517, 522, 591; 560/232

[56] References Cited

U.S. PATENT DOCUMENTS

| | | | |
|---|---|---|---|
| 3,579,551 | 5/1971 | Craddock et al. | 562/522 X |
| 3,816,489 | 6/1974 | Craddock et al. | 562/522 |
| 4,334,092 | 6/1982 | Knifton | 562/517 |
| 4,612,387 | 9/1986 | Feitler | 560/232 |
| 4,622,423 | 11/1986 | Burke | 562/522 |
| 4,640,802 | 2/1987 | Drent | 260/410.9 R |
| 4,659,518 | 4/1987 | Rizkalla | 260/413 |
| 4,780,334 | 10/1988 | Burke | 427/248.1 |
| 4,788,333 | 11/1988 | Burke | 562/517 |
| 4,939,298 | 7/1990 | Burke | 562/591 |

FOREIGN PATENT DOCUMENTS 55-51037  4/1980  Japan .

OTHER PUBLICATIONS

Catal. Rev.—Sci. Eng., vol. 23 (1 & 2), pp. 89–105, (1981) Marcel Dekker, Inc.

*Primary Examiner*—Arthur C. Prescott

[57] ABSTRACT

A process for the preparation of adipic acid from pentenoic compounds by hydrocarboxylation using an iridium catalyst, an iodide promoter, water, carbon monoxide and a carboxylic acid solvent.

9 Claims, No Drawings

PROCESS FOR THE MANUFACTURE OF ADIPIC ACID

REFERENCE TO EARLIER APPLICATION

This application is a continuation-in-part of application Ser. No. 07/804,559 filed Dec. 10, 1991, now abandoned.

FIELD OF THE INVENTION

This invention relates to a process for the manufacture of adipic acid.

BACKGROUND OF THE INVENTION

The dominant commercial process for the manufacture of adipic acid involves the air-oxidation of cyclohexane to form a mixture of cyclohexanol and cyclohexanone, which is subsequently oxidized with nitric acid to form a mixture of carboxylic acids, including adipic acid.

Another patented process (Burke U.S. Pat. No. 4,788,333 and U.S. Pat. No. 4,788,334) for making adipic acid involves the hydrocarboxylation of pentenoic acids and their esters. Pentenoic acids and their esters, and in particular 3-pentenoic acid, are available from butadiene and butadiene derived feedstocks by metal catalyzed hydrocarboxylation. Such processes have the potential of providing high yield, high rate, low pollution processes for the manufacture of adipic acid.

In the hydrocarboxylation of 3-pentenoic acid and its esters, undesirably high levels of branched products are formed. Burke (U.S. Pat. No. 4,788,333) has disclosed that, for the production of adipic acid by the hydrocarboxylation of pentenoic acids, high linear selectivity is obtained when an iodide promoted rhodium catalyst is employed in conjunction with selected halocarbon solvents. While better linear selectivity is obtained in halocarbon solvents, their use results in additional costs associated with the containment, recovery and recycle of these volatile, environmentally hazardous solvents.

Burke discloses in U.S. Pat. No. 4,939,298, that branched diacids can be isomerized to adipic acid by heating in the presence of carbon monoxide and an iodide or bromide promoted rhodium catalyst.

The most commonly used promoters for metal catalyzed hydrocarboxylation also promote the conversion of pentenoic acids and esters to valerolactones. These lactones normally consist primarily of gamma-valerolactone (hereinafter referred to as valerolactone). Valerolactone can be hydrocarboxylated to adipic acid as described in Burke EPO published application 0395038, but there are costs and yield losses associated with such processes.

In U.S. Pat. No. 4,788,334 Burke discloses that the rate of hydrocarboxylation of pentenoic esters in selected aromatic and halocarbon solvents is accelerated by the addition of an aliphatic or aromatic acid having a pKa in the range of 4.2 to 5.2.

Craddock et al. (U.S. Pat. No. 3,816,489) have disclosed a process for the production of terminal carboxylic acids from ethylenically unsaturated compounds by hydrocarboxylation "in the presence of catalyst compositions essentially comprising iridium compounds and complexes, together with an iodide promoter in critical proportions". U.S. Pat. No. 3,816,488 discloses that similar results can be obtained using rhodium catalysts. The preferred reaction solvents are monocarboxylic acids having 2 to 20 carbon atoms.

The process of this invention seeks to overcome the disadvantages of the prior art by providing a high yield, high rate, low-pollution process for the manufacture of adipic acid from pentenoic acids and esters. The process of this invention gives high linear selectivity while avoiding the use of halocarbon solvents and results in the formation of relatively low levels of valerolactone.

SUMMARY OF THE INVENTION

This invention provides a process for the production of adipic acid which comprises forming a reaction mixture comprising (a) at least one pentenoic compound selected from the group consisting of a pentenoic acid, a methyl ester of a pentenoic acid, and an ethyl ester of a pentenoic acid, (b) carbon monoxide, (c) at least about a stoichiometric amount of water, based on the pentenoic compound, (d) a carboxylic acid solvent selected from aliphatic $C_2-C_{20}$ monocarboxylic acids, aliphatic $C_4-C_{20}$ dicarboxylic acids, benzoic acid and substituted benzoic acids and mixtures thereof, and (e) an iridium-containing catalyst and an iodide compound that are both soluble in the combination of other components, the concentration of iridium being about 100 to 5,000 parts per million of the reaction mixture, the concentration of iodide being about 500 to 8,000 parts per million of the reaction mixture, and the molar ratio of iodide to iridium being about 1:1 to 5:1, and reacting this mixture at a temperature in the range of 100°–220° C. and a pressure in the range of about 0 to 2000 psig.

DETAILED DESCRIPTION OF THE INVENTION

This invention provides an efficient, low pollution route to adipic acid based on the hydrogen iodide promoted, iridium catalyzed hydrocarboxylation of selected pentenoic compounds. In the hydrocarboxylation of 3-pentenoic acid, it has been found that the use of iridium catalysts provides higher reaction rates, higher yields of adipic acid at high conversion of the starting material, and high product linearity in carboxylic acid solvents. In a continuous commercial process higher one pass yields and higher overall yields of adipic acid will result in higher productivity.

One critical feature of this process is the use of relatively low molar ratios of iodide promoter to iridium in order to maintain high selectivity to linear products while minimizing the production of valerolactone and saturated by-products. Because of the corrosivity of iodide, the use of lower amounts of iodide is an advantage in itself. Another crucial feature of this process is its suitability for use in conjunction with carboxylic acid solvents. The use of carboxylic acid solvents not only simplifies processing, but eliminates the need for the handling and containment of hazardous halocarbon solvents.

Suitable substrates for the process of this invention include 2-pentenoic acid, 3-pentenoic acid, 4-pentenoic acid and the esters of these carboxylic acids. Examples of esters which can be employed in the process of this invention include methyl and ethyl esters. Feedstocks which consist primarily of 3-pentenoic acid or its esters are preferred for reasons of cost and availability. Feedstocks which consist primarily of 3-pentenoic acid are most preferred due to their ease of preparation. Anhydrides of pentenoic acids may also be beneficially employed in the process of this invention as long as sufficient water for both the hydrolysis of the anhydride and the hydrocarboxylation is present. When all or part of the feed is a pentenoic acid ester the product may contain adipic acid monoester which can be hydrolyzed in situ or in a subsequent step to give adipic acid. When the ester is to be hydrolyzed in situ, sufficient water for both the hydrolysis of the ester and the hydrocarboxylation should be present. In general the initial concentration of the pentenoic compound will be between 5 and 50% by weight of the reaction mixture in a batch process, and between 5 and 50% by weight of the feed in a continuous process. Preferably, the loading of the pentenoic compound is between 10 and 30% by weight.

The iridium catalyst can be provided from any source or by any material which will produce iridium ions under hydrocarboxylation conditions, i.e. iridium materials that are soluble in the other components of the reaction mixture. Among the materials which can be employed as the source of the iridium are iridium metal, iridium salts, iridium oxides, iridium carbonyl compounds, organoiridium compounds, coordination compounds of iridium and mixtures thereof. Specific examples of such compounds include, but are not limited to, iridium(III) chloride and its hydrates, iridium(III) bromide and its hydrates, iridium(III) iodide, iridium(III) oxide, iridium(IV) oxide, iridium(III) acetylacetonate, iridium(I) dicarbonyl acetylacetonate, iridium(III) nitrate, iridium(III) ethylhexanoate and dodecacarbonyl tetrairidium.

Preferred sources of iridium catalyst include iridium(III) chloride and its hydrates, iridium(III) iodide, and iridium(I) dicarbonyl acetylacetonate.

Suitable concentrations of iridium are in the range of about 100 ppm to 5000 ppm (parts per million) based on the weight of the reaction mixture although higher levels may be employed. Preferably, the concentration of iridium is in the range of 400 ppm to 4000 ppm, more preferably 800 ppm to 2000 ppm.

The iridium catalyst, which can be preformed or formed in situ, must be promoted by a source of iodide that is soluble in the other components of the reaction mixture in order to achieve satisfactory results. Although it is generally preferable to keep the concentration of iodide promoter below about 8,000 ppm total iodide based on the weight of the reaction mixture, the absolute level of iodide is not as critical as the molar ratio of iodide to iridium. Iodide to iridium ratios between about 1 and 5 may be beneficially employed in the process of this invention. Iodide to iridium ratios between 1 and 3 are preferred and ratios between 2 and 3 are most preferred. When iodide to iridium ratios greater than about 3:1 are employed, it is advantageous to employ lower iridium concentrations. This serves to reduce the total concentration of free hydrogen iodide and thus reduce the overall corrosivity of the reaction mixture.

Also, although the amount of valerolactone formed in this process is dependent on a number of factors, high free hydrogen iodide concentration tends to increase the amount of valerolactone formed. When iodide to iridium ratios of less than 2:1 are employed, it is believed that, in order to optimize the catalytic activity of the iridium, other ligands should be present in sufficient amounts to fill the iridium coordination sphere. Examples of such ligands are chloride and bromide.

The iodide promoter can be provided by hydrogen iodide, iodine, alkali metal iodides, alkaline earth metal iodides, organic iodides, or any other source which will provide hydrogen iodide under hydrocarboxylation conditions. Preferred sources of iodide include hydrogen iodide, aqueous solutions of hydrogen iodide, acetyl iodide, 4-iodobutyl acetate, aryl iodides, $C_1$–$C_{10}$ alkyl iodides, such as methyl iodide, iodoethane, 1-iodopropane, 2-iodopropane, 1-iodobutane, 2-iodobutane, 1,4-diiodobutane, and iodoheptane. The iodide and iridium can be present in the same compound, e.g., as in iridium(III) iodide. The most preferred sources of iodide promoter are hydrogen iodide, aqueous hydrogen iodide, methyl iodide and iodobutanes.

About a molar equivalent of water based on the pentenoic compound is necessary for high conversion of the pentenoic compound; therefore at least about a stoichiometric amount of water is employed. Although an excess of water may be present in the process of this invention, large excesses should be avoided. In general, the concentration of water at the start of the hydrocarboxylation reaction should be no more than about 15% by weight of the total reaction mixture. In order to obtain higher reaction rates and better product linearity it is preferred that the concentration of water at the start of the hydrocarboxylation reaction be no more than about 10% by weight.

Reaction temperatures in the range of 100° to 220° C. may be employed in the practice of this invention. However, at lower temperatures the reaction rates are slower and the linear selectivity is somewhat less, while at temperatures above 220° C. significant decomposition of the product adipic acid can occur. In general, temperatures in the range of 130° to 220° C. are satisfactory, while 170° to 210° C. are preferred. Optimum reaction temperatures will vary depending on the nature of the solvent system employed.

Although higher pressures may be used, total pressures in the range of about 0 to 2000 pounds per square inch (psig) are most conveniently employed in the process of this invention. At constant temperature, the linear selectivity improves with decreasing pressule until values as high as about 85% are reached. Lower pressures therefore widen the temperature range where optimum yield to linear product may be achieved. Generally, the lowest possible pressure should be employed with catalyst stability at the reaction temperature in the specific solvent system and with the need to supply sufficient carbon monoxide for the reaction.

Suitable carboxylic acid solvents for the process of this invention include, but are not limited to, aliphatic $C_2$–$C_{20}$ monocarboxylic acids, aliphatic $C_4$–$C_{20}$ dicarboxylic acids, benzoic acid, and alkyl substituted benzoic acids. Preferred solvents are aliphatic $C_2$–$C_{20}$ monocarboxylic acids and aliphatic $C_5$–$C_8$ dicarboxylic acids. Mixtures of the monocarboxylic and dicarboxylic acids produced in the process of this invention are particularly useful as solvents for the process of this invention. Such mixtures contain valeric acid, methylbutyric acids, adipic acid, 2-methylglutaric acid, ethylsuccinic acid, and dimethyl-succinic acid as well as other components such as valerolactones. Solvent usually is present in the reaction mixture in the amount of about 40 to 94 percent by weight of the reaction mixture. It is often most convenient to use about 65 to 90 percent by weight of the initial reaction mixture.

It has also been found that hydrocarbon solvents may be beneficially employed in the iridium catalyzed hydrocarboxylation process of the present invention to produce dibasic acids with high selectivity for adipic acid. Hydrocarbon solvents may also be employed as co-solvents or diluents in conjunction with carboxylic acid solvents. Advantages associated with the use of a co-solvent or diluent include enhanced recovery of adipic acid and improved mobility of the process streams. Examples of hydrocarbon solvents which may be employed include, but are not limited to, cyclohexane, benzene, toluene and xylenes.

As mentioned above, pentenoic acids and their esters are most readily prepared from butadiene and butadiene derived feedstocks by metal catalyzed hydrocarboxylation. It has been found that metals, such as rhodium, which catalyze the hydrocarboxylation of butadiene and butadiene derived feedstocks are compatible with the process of this invention. Thus, the reaction mixtures obtained from the rhodium catalyzed hydrocarboxylation of butadiene and butadiene derived feedstocks can be used directly in the process of this invention without the need to remove the rhodium catalyst. In such cases, linear selectivity can be controlled by adjusting the ratio of iridium to rhodium. Generally, a molar ratio of iridium to rhodium of greater than about 2 to 1 is preferred.

EXAMPLES

The process of this invention is illustrated by the following examples. Experiments 1–17 were carried out in a 300 ml Hastelloy autoclave. Experiments 18 and 19 were carried out in a 100 ml Zirconium autoclave. The products were characterized by first esterifying the carboxylic acid components (by treatment with boron trifluoride in methanol at 90° C. for one hour), diluting with water, and then analyzing a methylene chloride extract by capillary gas chromatography using orthodichlorobenzene as the internal standard. The results, which were converted to moles and then normalized to 100%, are presented in Table 1. The time given in Table 1 represents the time from the completion of the addition of the pentenoic acid or ester.

EXAMPLE 1

The autoclave was charged with 141.5 grams of acetic acid, 0.65 grams of iridium(I) dicarbonyl acetyl acetonate, 0.84 grams 57% HI (57% aqueous hydrogen iodide solution), and 0.5 grams water to give a solution in which the molar ratio of iodide to iridium was 2:1. The autoclave was purged with CO to remove traces of air, and then heated to 190° C. under a CO pressure of 500–700 psig. The pressure was then adjusted to about 700 psig and a mixture of 48.0 grams of trans 3-pentenoic acid and 8.4 grams water was injected. The calculated initial iridium concentration after this addition was about 1800 ppm.

EXAMPLE 2

This reaction was run under the same conditions as described in Example 1 except that the pressure was adjusted to about 440 psig for the hydrocarboxylation reaction.

EXAMPLE 3

This reaction was run under the same conditions as described in Example 1 except that the pressure was adjusted to about 300 psig for the hydrocarboxylation reaction.

EXAMPLE 4

The autoclave was charged with 130 grams acetic acid, 0.116 grams of iridium trichloride, 0.187 grams 57% HI, and 0.5 grams water to give a solution in which the molar ratio of iodide to iridium was 4.3:1. The autoclave was purged with CO to remove traces of air, and then heated at 174° C. under about 730 psig CO pressure overnight. The temperature was then increased to 190° C. and the pressure was adjusted to about 700 psig prior to the injection of a mixture of 48.0 grams of trans 3-pentenoic acid and 8.4 grams water in 12 equal portions at 10 minute intervals. The calculated iridium concentration after the last addition was about 400 ppm.

EXAMPLE 5

This reaction was run under the same conditions as described in Example 4 except that: (a) the amounts of iridium trichloride and 57% HI were adjusted so that the molar ratio of iodide to iridium was 1.4:1; and, (b) a mixture of 24.0 grams of trans 3-pentenoic acid and 4.2 grams water were injected in 6 equal portions at 10 minute intervals.

EXAMPLE 6

This reaction was run under the same conditions as described in Example 1 except that the amounts of iridium(I) dicarbonyl acetyl acetonate and 57% HI were adjusted so that the initial iridium concentration was about 3600 ppm.

EXAMPLE 7

This reaction was run under the same conditions as described in Example 1 except that: (a) the amount of acetic acid was reduced to 130 grams; (b) the amounts of iridium(I) dicarbonyl acetyl acetonate and 57% HI were adjusted so that the initial iridium concentration was about 400 ppm; and (c) the reaction temperature was 170° C.

EXAMPLE 8

This reaction was run under the same conditions as described in Example 7.

EXAMPLE 9

This reaction was run under the same conditions as described in Example 1 except that the amount of water added with the 3-pentenoic acid was doubled.

EXAMPLE 10

This reaction was run under the same conditions as described in Example 9 except that the amount of 3-pentenoic acid was reduced to 8 grams. As a result of the reduced 3-pentenoic acid charge, the calculated initial iridium concentration after the 3-pentenoic acid addition was about 2139 ppm.

EXAMPLE 11

This reaction was run under the same conditions as described in Example 4 except that: (a) the amounts of iridium chloride and 57% HI were adjusted so that the molar ratio of iodide to iridium was 2.9:1 and the initial iridium concentration after the 3-pentenoic acid addition was 750 ppm; and, (b) the amount of water added with the 3-pentenoic acid was increased by 25%.

EXAMPLE 12

This reaction was run under the same conditions as described in Example 1 except that: (a) the amount of acetic acid was reduced to 130 grams; and, (b) the amounts of iridium(I) dicarbonyl acetyl acetonate and 57% HI were adjusted so that the initial iridium concentration was about 800 ppm.

EXAMPLE 13

The autoclave was charged with 130 grams acetic acid as solvent, 0.233 grams of iridium trichloride, 0.5 grams 57% HI, and 0.5 grams water to give a solution in which the molar ratio of iodide to iridium was 2.9:1. The autoclave was purged with CO to remove traces of air, and then heated at 170° C. under about 680 psig CO for 2 hours. The temperature was then increased to 190° C. and the pressure was adjusted to about 700 psig prior to the injection of a mixture of 20 grams of trans methyl 3-pentenoate, 3.5 grams water, and 5 grams of acetic acid in 5 equal portions at 10 minute intervals. The calculated iridium concentration after the addition was about 939 ppm.

EXAMPLE 14

The autoclave was charged with 130 grams acetic acid, 0.186 grams of iridium trichloride, 1.0 gram of a rhodium catalyst solution containing 2.34% rhodium and in which the molar ratio of iodide to rhodium was 1.9:1 (prepared by dissolving the appropriate quantities of rhodium(II) acetate dimer and rhodium(III) iodide in 70% aqueous acetic acid and heating at 100° C. under about 100 psig CO pressure for about four hours), 0.25 grams of 57% HI, and 0.25 grams of water to give a solution in which the molar ratio of iodide to (iridium plus rhodium) was 1.8:1. The autoclave was purged with CO to remove traces of air, heated to 180° C. under about 700 psig CO pressure and held overnight. The temperature was increased to 190° C. and the pressure adjusted to about 700 psig and a mixture of 24.0 grams of trans 3-pentenoic acid, 7.0 grams water and 2.0 grams of acetic acid was injected in 6 equal portions at 10 minute intervals. The calculated initial iridium concentration after this addition was about 727 ppm and the calculated initial rhodium concentration was about 142 ppm.

EXAMPLE 15

The reaction was run under the same conditions as described in Example 4 except that: (a) the amounts of iridium chloride and 57% HI were adjusted so that the molar ratio of iodide to iridium was 2.9, and the iridium concentration was about 913 ppm; and (b) a mixture of 24 grams of 2-pentenoic acid and 5 grams water were injected in 6 equal portions at ten minute intervals.

EXAMPLE 16

The reaction was run under the same conditions as described in Example 4 except that: (a) the amounts of iridium chloride and 57% HI were adjusted so that the molar ratio of iodide to iridium was 1.4:1, and the iridium concentration was about 2119 ppm; and, (c) a total of 8 grams of 4-pentenoic acid and 1.6 grams water were injected in 2 equal portions at 10 minute intervals.

EXAMPLE 17

The reaction was run under the same conditions as described in Example 1 except that the temperature was 210° C.

EXAMPLE 18

A 100 ml Zirconium autoclave was charged with 76 grams of acetic acid, 0.23 grams of iridium (I) dicarbonyl acetyl acetonate, 0.30 grams of 57% aqueous hydrogen iodide solution and 1.1 grams of water. The autoclave was purged with carbon monoxide to remove traces of air and then heated to 125° C. The pressure was then adjusted to 50 psig with carbon monoxide and a mixture of 5.5 grams of trans-3-pentenoic acid and 1.0 grams of water was added via pump over 2 minutes.

EXAMPLE 19

The reaction was run under the same conditions as described in Example 8 except that the pressure was adjusted to 700 psig.

TABLE 1

| Ex. | Time (min) | Temp. (°C.) | (psig) | I:Ir | Ir (ppm) | AA | 3-PA | 2-PA + 4-PA | VL | LIN. | Yield Index |
|---|---|---|---|---|---|---|---|---|---|---|---|
| 1 | 80 | 190 | 700 | 2:1 | 1800 | 64.6 | 0.2 | 0.2 | 15.2 | 84.0 | 89.6 |
| 2 | 80 | 190 | 440 | 2:1 | 1800 | 61.6 | 0.2 | 0.8 | 15.9 | 82.6 | 87.6 |
| 3 | 80 | 190 | 300 | 2:1 | 1800 | 51.0 | 0.3 | 0.4 | 19.5 | 79.3 | 76.8 |
| 4 | 80 | 190 | 700 | 4.1:1 | 400 | 62.3 | 2.6 | 4.0 | 15.1 | 82.7 | 95.4 |
| 5 | 80 | 190 | 700 | 1.4:1 | 400 | 70.0 | 0.1 | 0.9 | 7.8 | 85.6 | 88.2 |
| 6 | 80 | 190 | 700 | 2:1 | 3600 | 58.1 | 0.1 | 0.1 | 14.3 | 81.3 | 80.4 |
| 7 | 80 | 170 | 700 | 2:1 | 400 | 30.4 | 53.7 | 4.8 | 3.4 | 81.6 | 97.5 |
| 8 | 1020 | 170 | 700 | 2:1 | 400 | 71.0 | 0.1 | 1.4 | 8.1 | 82.4 | 94.4 |
| 9 | 80 | 190 | 700 | 2:1 | 1800 | 60.4 | 0.1 | 1.4 | 14.3 | 80.5 | 86.9 |
| 10 | 80 | 190 | 700 | 2:1 | 2139 | 54.0 | 0.0 | 0.4 | 15.9 | 73.6 | 83.9 |
| 11 | 80 | 190 | 700 | 2.9:1 | 750 | 69.2 | 0.2 | 1.6 | 10.4 | 83.8 | 92.8 |
| 12 | 80 | 190 | 700 | 2:1 | 800 | 69.9 | 0.2 | 1.7 | 11.9 | 84.8 | 94.8 |
| 13 | 80 | 190 | 700 | 2.9:1 | 939 | 62.5 | 9.9 | 3.2 | 5.4 | 85.0 | 91.9 |
| 14 | 80 | 190 | 700 | 1.8:1** | 727*** | 65.4 | 0.3 | 2.2 | 12.5 | 81.8 | 92.8 |
| 15 | 80 | 190 | 700 | 2.9:1 | 913 | 30.6 | 2.6 | 40.5 | 2.5 | 82.5 | 64.0 |
| 16 | 40 | 190 | 700 | 1.4:1 | 2119 | 71.6 | 0.2 | 1.1 | 8.7 | 88.5 | 88.8 |
| 17 | 80 | 210 | 700 | 2:1 | 1800 | 57.6 | 0.3 | 0.2 | 17.4 | 82.0 | 82.8 |
| 18 | 240 | 125 | 50 | 2:1 | 1500 | 70.4 | 0.5 | 2.0 | 2.5 | 81.4 | 89.1 |
| 19 | 240 | 125 | 700 | 2:1 | 1500 | 47.8 | 21.4 | 2.5 | 3.5 | 70.3 | 91.9 |

AA = Adipic Acid
2-PA = 2-Pentenoic Acid
3-PA = 3-Pentenoic Acid
4-PA = 4-Pentenoic Acid
VL = Valerolactone
Yield Index = AA/(AA + Valeric Acid + Methylbutyric Acid)
Linearity = AA/(AA + Methylglutaric Acid + Ethylsuccinic Acid + Dimethyl Succinic Acid)
*Mole % of all products plus unreacted starting material.
**Molar ratio of iodide to iridium plus rhodium.
***Reaction mixture contained 727 ppm iridium and 142 ppm rhodium.

I claim:

1. A process for the production of adipic acid which comprises forming a reaction mixture comprising (a) at least one pentenoic compound selected from the group consisting of a pentenoic acid, a methyl ester of a pentenoic acid, and an ethyl ester of a pentenoic acid, (b) carbon monoxide, c) at least about a stoichiometric amount of water, based on the pentenoic compound, (d) a carboxylic acid solvent selected from aliphatic $C_2$-$C_{20}$ monocarboxylic acids, aliphatic $C_4$-$C_{20}$ dicarboxylic acids, benzoic acid and substituted benzoic acids and mixtures thereof, and (e) an iridium-containing catalyst and an iodide compound that are both soluble in the combination of other components, the concentration of iridium being about 100 to 5,000 parts per million of the reaction mixture, the concentration of iodide being about 500 to 8,000 parts per million of the reaction mixture, and the molar ratio of iodide to iridium being about 1:1 to 5:1, and reacting this mixture at a temperature in the range of 100°-220° C. and a pressure in the range of about 0 to 2000 psig.

2. The process of claim 1 wherein the temperature is between 170° and 210° C. and the iridium concentration is between 800 and 2000 ppm.

3. The process of claim 2 wherein the molar ratio of iodide to iridium at about 1:1 to 3:1.

4. The process of claim 3 wherein the pentenoic compound is 3-pentenoic acid.

5. The process of claim 4 wherein the solvent is a mixture of the monocarboxylic and dicarboxylic acids produced in the process.

6. The process of claim 5 wherein the molar ratio of iodide to iridium is about 2:1 to 3:1.

7. The process of claim 1 in which a hydrocarbon co-solvent is employed.

8. The process of claim 1 in which the solvent is selected from aliphatic $C_2$ to $C_{20}$ monocarboxylic acids and aliphatic $C_5$-$C_8$ dicarboxylic acids and mixtures thereof.

9. The process of claim 1 wherein the temperature is in the range of 130°-220° C. and the pressure is in the range of about 300 to 2000 psig.

* * * * *